United States Patent [19]
Castelli et al.

[11] 4,188,322
[45] Feb. 12, 1980

[54] PROCESS FOR THE PREPARATION OF 6-HALO-PREGNANES

[75] Inventors: Pier P. Castelli, Monza; Bruno Romanò, Besana Brianza, both of Italy

[73] Assignee: Blasinachim S.p.A., Milan, Italy

[21] Appl. No.: 900,886

[22] Filed: Apr. 28, 1978

[51] Int. Cl.² ............................................. C07J 71/00
[52] U.S. Cl. .................. 260/239.55 R; 260/239.55 D
[58] Field of Search ................ 260/239.55, 239.55 D, 260/239.55 R

[56] References Cited
U.S. PATENT DOCUMENTS

| | | | |
|---|---|---|---|
| 3,465,011 | 9/1969 | Stein et al. | 260/239.55 |
| 3,513,160 | 5/1970 | Bright et al. | 260/239.55 |

*Primary Examiner*—Elbert L. Roberts
*Attorney, Agent, or Firm*—Scully, Scott, Murphy & Presser

[57] ABSTRACT

The invention relates to a new process for the preparation of 6α-halo-3-keto-$\Delta^{1,4}$-pregnadiene-derivatives in two-steps-synthesis affording directly 6α-halo-derivatives by reacting 3-keto-9β,11β-oxido-$\Delta^{1,4}$-pregnadiene-derivatives with a suitable acylating or etherifying agent to give the corresponding new 3-enol-derivatives which are finally halogenated by using a suitable halogenating agent.

9 Claims, No Drawings

PROCESS FOR THE PREPARATION OF 6-HALO-PREGNANES

The present invention is concerned with a new process for the synthesis of highly active steroids compounds such as the 6α-halo-derivatives, and more particularly the 6α-fluoro-derivatives, of $\Delta^{1,4}$-3keto pregnadienes.

It is known that such derivatives are usually prepared by treatment with halogenated electrophilic reagents of $\Delta^{3,5}$-diene-3-ol esters or ethers deriving from $\Delta^4$-3-keto steroids.

Now we have found that the same route can be successfully carried out starting from $\Delta^{1,4}$-3-keto compounds.

It is known from the literature (U.S. Pat. No. 3,506,650 and U.S. Pat. No. 3,629,299) that it is possible to enolize a $\Delta^{1,4}$-3-keto grouping only in the limited class of derivatives having an 11-keto group. This fact involves complicate process to transform the 11-keto group in the more active 11β-hydroxy compounds with or without a 9-halo substituent. We have surprisingly found that 3-enol-derivatives of 9β,11β-oxido-$\Delta^{1,4}$-pregnadiene-3-ones, i.e. the 9β,11β-oxido-$\Delta^{1,3,5}$-pregnatriene-3-ol 3-esters or 3-ethers, can be prepared in high yields by reaction of the 9β,11β-oxido-steroid with a suitable acylating or etherifying agent, such as acyl anhydrides isopropenyl acetate, trialkylortoformates, under controlled operating conditions. The 3-enol-derivatives, once formed, are then halogenated to the 6-halo-derivatives by using a suitable halogenating agent, such as N-haloamides, perchloryl fluoride etc.

The halogenation reaction can be carried out on the 3-enol-derivative previously isolated or directly on the enolization reaction mixture. In this case it is sufficient, after the enolization reaction is completed, to carefully remove most of the solvents or reactants under vacuum and dissolve the residue in the required solvent for the next step.

It is an object of this invention to provide novel steroid intermediates such as 3-enolesters or 3-enolethers of 9β,11β-oxido-$\Delta^{1,4}$-3-ketosteroids.

It is another object to provide a simplified procedure for forming the 6-halo-derivatives of $\Delta^{1,4}$-3-ketosteroids.

It is an advantage of this invention that the 6-halo-derivative thus produced is generally the epimer α-oriented or at least a mixture in which the α-epimer is the predominant.

On opening in the conventionally manner the epoxy ring of such 6α-halo-$\Delta^{1,4}$-3-keto-derivatives with halogenidric acids are then easily obtained the corresponding highly active 6α,9α-dihalo-11β-hydroxy-$\Delta^{1,4}$-pregnadiene-3-ones. If the end product desired is a 6α-fluoro-derivative without substituent in the 9-position, the epoxide opening is performed with halogenidric acids different from hydrofluoric acid and submitting the resultant 9-halo-derivative to dehalogenation by means of the methods known in the art.

The new process object of this invention is represented by the following schema:

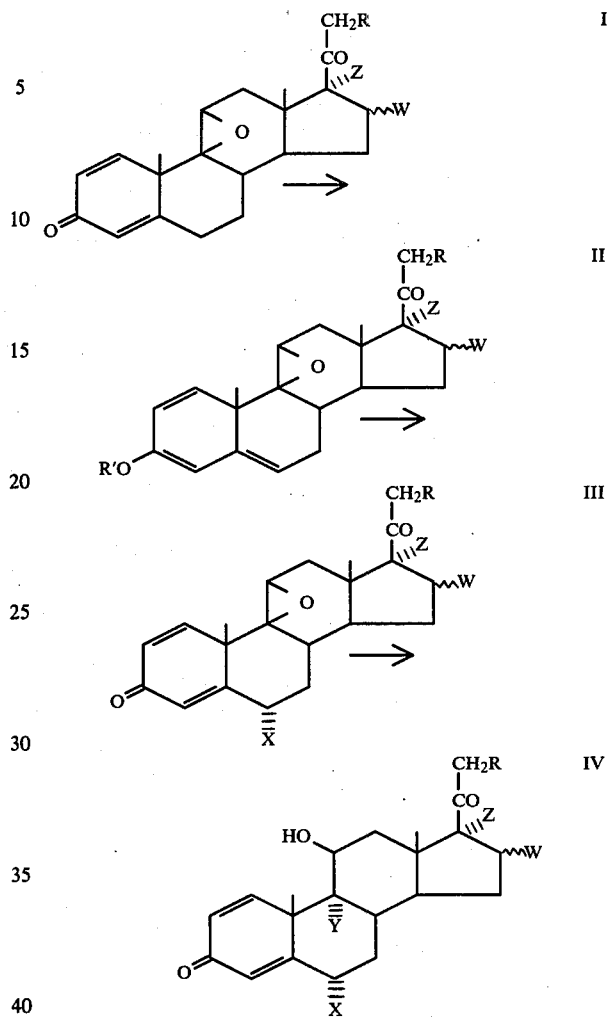

Wherein:
R is hydrogen or hydroxy or acyloxy;
R' is acyl or alkyl;
Z is hydrogen or hydroxy or acyloxy;
W is hydrogen or hydroxy or methyl;
X is halogen;
Y is hydrogen or halogen;
In particular:

When in the starting compound (I) Z is hydroxy and W is hydroxy α-oriented, these cis-diols can be condensed with a molecula of a ketone or an aldehyde to form a 16α,17α-acetal or ketal group; when R, or Z, or W α-oriented are present in the starting compound (I) as hydroxy, and the enolization process of the $\Delta^{1,4}$-3-ketone consists in an enolesterification, the above groups undergo the acylation reaction and are present in the formula II, III and IV as acyloxy groups in which the acyl residue is the same of the enolesterifying agent employed.

Such acyloxy groups, in view of the end desired product, can be maintained or removed by means of the conventional procedure to give the free hydroxy derivatives.

The following examples illustrate the invention.

EXAMPLE 1

(a) A solution of 9β,11β-oxido-16α,17α,21-trihydroxy-pregna-1,4-diene-3,20-dione 16,17-acetonide 21-acetate (10 gr.) and p-toluensulfonic acid monohydrate (1.5 gr.) in isopropenyl acetate (200 ml) is slowly distilled during 10 hours, the volume of the reaction mixture being maintained above 100 ml by periodic addition of isopropenyl acetate. The solution is cooled to room temperature and 10 gr. of solid sodium bicarbonate is added.

The remaining reagent is removed by distillation under vacuum. The residue is shaken with ether and water, the layers are separated and the aqueous layer is extracted twice with ether. The combined extracts are washed with water then with saturated sodium chloride solution and dried over anhydrous sodium sulfate. The solvent is removed under vacuum and the residue is crystallized from methanol to give 3,21-diacetoxy-9β,11β-oxido-16α,17α-dihydroxy-pregna-1,3,5-triene-20-one 16,17-acetonide (10 gr.):

M.P. 182° C.

$\lambda_{max}^{EtOH}$ 211 mμ and 331 mμ ($\epsilon$=10,350 and 5,600 respectively)

$[\alpha]_D$ −195° (Diox.)

(b) Into a solution of the above compound (9.5 gr.) in 400 ml of tetrahydrofuran containing a 20 percent of water, perchloryl fluoride is gently bubbled at room temperature for 45 min. Excess of reagent is removed by bubbling into the mixture nitrogen for 30 min. Then most of the solvent is eliminated by distillation under reduced pressure. The residue is extracted with ether and the combined extracts are washed with a 5% solution of sodium bicarbonate and then with water. After drying over anhydrous sodium sulfate the solvent is removed under vacuum and the residue is tritured with methanol to give 6α-fluoro-9β,11β-oxido-16α,17α,21-trihydroxy pregna-1,4-diene-3,20-dione 16,17-acetonide 21-acetate (7.0 gr.)

M.P. 232° C. (with dec.)

$\lambda_{max}^{EtOH}$ 246 mμ ($\epsilon$=15,900)

$[\alpha]_D$+59° (Diox.)

By treatment of the above compound with hydrogen fluoride in the usual manner Fluocinonide is obtained which, if desired, after deacylation, gives Fluocinolone acetonide, identical in all chemicophysical characteristics with an autentic sample prepared according to the known procedures.

EXAMPLE 2

Five grams of 9β,11β-oxido-17α,21-dihydroxypregna-1,4-diene-3,20-dione are submitted to react with isopropenyl acetate exactly as described in the Example 1a. After the elimination of the reagent, the residue is dissolved in aqueous tetrahydrofuran (200 ml), and treated with perchloryl fluoride according to the procedure described in the Example 1b, thus obtaining 6α-fluoro-9β,11β-oxido-17α,21-dihydroxypregna-1,4-diene-3,20-dione 17,21-diacetate (3.4 gr.):

M.P. 224° C. (with dec.)

$\lambda_{max}^{EtOH}$ 247 mμ ($\epsilon$=15,300)

$[\alpha]_D$+3.14° (Diox.)

The above compound treated with hydrogen fluoride in the usual manner gives 6α,9α-difluoro-prednisolone diacetate, from which, after alkaline deacylation 6α,9α-difluoroprednisolone is obtained, identical in all chemico-physical characteristics with an autentic sample prepared according to the known procedures.

EXAMPLE 3

Twelve grams of 9β,11β-oxido-16α-methyl-17α,21-dihydroxypregna-1,4-diene-3,20-dione are treated exactly as described in the Example 2. The crude 6α-fluoro-9β,11β-oxido-16α-methyl-17α,21-dihydroxy-pregna-1,4-diene-3,20-dione 17,21-diacetate (8.7 gr.) is suspended in a mixture of methylene chloride-methanol and treated under nitrogen stream with a catalytic amount of methanolic potassium hydroxide at room temperature for 90 min. After neutralization with aqueous acetic acid the solution is concentrated under reduced pressure, and the residue is crystallized from methanol to yield 6α-fluoro-9β,11β-oxido-16α-methyl-17α,21-dihydroxypregna-1,4-diene-3,20-dione (6.5 gr.):

M.P. 268° C. (with dec.)

$\lambda_{max}^{MeOH}$ 247 mμ ($\epsilon$=16,150)

$[\alpha]_D$+31° (DMF)

The treatment of the above compound with hydrogen fluoride in the conventional manner gives Flumethasone, identical in all chemico-physical characteristics with an autentic sample prepared according to the known procedures.

EXAMPLE 4

Two grams of 6α-fluoroderivative prepared in the Example 1b are added portionwise to 10 ml of aqueous hydrobromic acid (48%) previously cooled at −15° C. and maintained under vigorous stirring. The mixture is kept for about 2 hr. at 0° C. and then poured cautiously into an excess of ice-cold solution of sodium carbonate. Extraction with methylene chloride and crystallisation from methylene chloride-methanol furnish 6α-fluoro-9α-bromo-11β,16α,17α,21-tetrahydroxypregna-1,4-diene-3,20-dione 16,17-acetonide 21-acetate (2.15 gr.)

M.P. 218° C. (with dec.)

$[\alpha]_D$+106.4° (Diox.)

$\lambda_{max}^{EtOH}$ 241 mμ ($\epsilon$=14,600)

Submitting the above compound to a 9-debromination procedure according to known methods the 21-acetate of Flunisolide is obtained.

EXAMPLE 5

(a) To a suspension of 9β,11β-oxido-16α,17α,21-trihydroxypregna-1,4-diene-3,20-dione 16,17-acetonide 21-acetate (10 gr.) in tetrahydrofurane (50 ml), methyl orthoformate (10 ml) and absolute methanol (20 ml), p-toluen-sulfonic acid (400 mg) is added and the mixture is stirred at room temperature.

The starting material dissolves and the reaction mixture is stirred for a total of 6 hr.

Pyridine (1 ml) is added and the solution is distilled under reduced pressure. The residue is crystallized from methanol to give 3-methoxy-9β,11β-oxido-16α,17α,21-trihydroxypregna-1,3,5-triene-20-one 16,17-acetonide 21-acetate (5 gr.):

M.P. 172° C.

$\lambda_{max}^{EtOH}$ 250 mμ and 320 mμ ($\epsilon$=2,900 and 4,150 respectively)

$[\alpha]_D$ −164° (Diox.)

(b) Into a solution of the above compound (3 gr.) in pyridine (60 ml) perchloryl fluoride is bubbled for 10 min. After removal of the excess of reagent by bubbling nitrogen the solution is poured into ice water. The crystalline solid is filtered, well washed with water, dried and crystallized from methanol to give 6α-fluoro-9β,11β-oxido-16α,17α,21-trihydroxypregna-1,4-diene- 3,20-dione 16,17-acetonide 21-acetate (2 gr.) identical with the one obtained in the Example 1b.

(c) A solution of the above 3-methyl-enolether obtained at point (a) (2 gr.) in acetone (40 ml) is treated with anhydrous sodium acetate (0.4 gr.), water (6 ml) and N-chlorosuccinimide (1.06 gr.). The mixture is stirred overnight then poured into ice water. The precipitate is collected by filtration, well washed with water, dried and tritured with methanol to give 6α-chloro-9β,11β-oxido-16α,17α21-trihydroxypregna-1,4-diene-3,20-dione 16,17-acetonide 21-acetate (1.5 gr.):

M.P. 199° C.

$\lambda_{max}$ 247 mμ (ε=14,500)

$[\alpha]_D$+53 (Diox.)

EXAMPLE 6

Exactly as described in the Example 5a the 21-acetate of 9β,11β-oxido-16α-methyl-21-hydroxypregna-1,4-diene-3,20-dione is submitted to react with methyl orthoformate. After removal of most of the solvents under vacuum the residue is dissolved in pyridine and treated with perchloryl fluoride as described in the Example 5b, to give 6α-fluoro-9β,11β-oxido-16α-methyl-21-hydroxypregna-1,4-diene-3,20-dione 21-acetate:

M.P. 178° C.

$[\alpha]_D$+87° (Diox.)

By reaction with hydrogen fluoride in the conventional manner the above compound is converted in the 21-acetate of Diflucortolone.

EXAMPLE 7

Operating as described in the Example 2 and starting from the 9β,11β-oxido-16β-methyl-17α-hydroxypregna-1,4-diene-3,20-dione (5 gr.), the 17-acetate of 6α-fluoro-9β,11β-oxido-16β-methyl-17α-hydroxypregna-1,4-diene-3,20-dione (3.5 gr.) is obtained:

M.P. 212° C. (with dec.)

$\lambda_{max}^{EtOH}$ 246 mμ (ε=15,000)

$[\alpha]_D$+41.2° (Diox.)

By means of the conventional procedures to introduce the 21-hydroxylated function and opening of 9β,11β-oxido with hydrogen fluoride, the above compound is converted in Diflorasone, identical in all chemicophysical characteristics with an autentic sample prepared according to the known procedures.

We claim:

1. A process for the preparation of a 6α-halo-3-keto-Δ$^{1,4}$-pregnadiene-derivative of the structure:

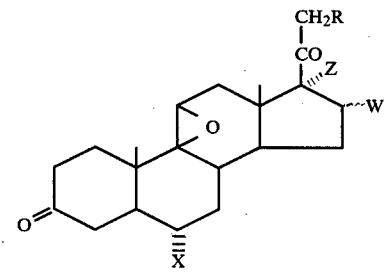

wherein R and Z are hydrogen, or hydroxy or acyloxy derived from carboxylic acids containing up to 9 carbon atoms; or when Z is hydroxy and W is hydroxy α-oriented can represent together the group

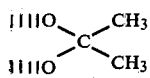

W is hydrogen or hydroxy or methyl; X is halogen, preferably fluorine and chlorine, which comprises reacting a 3-keto-Δ$^{1,4}$-pregnadiene-derivative of the structure I:

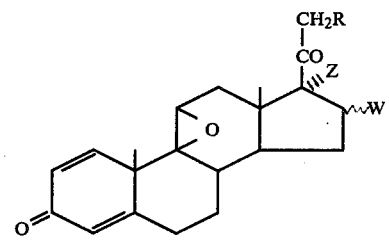

in which R,Z and W have the above meaning, with a suitable acylating or etherifying agent, such as acyl anhydrides, isopropenyl acetate, trialkyl orthoformates in the presence of acid catalysts, such as p-toluenesulfonic acid, to give the corresponding 3-enol-derivatives of the structure II:

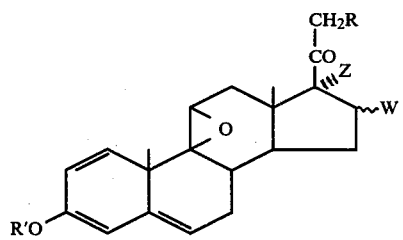

wherein R,Z and W have the above meaning and R' is a lower acyl or alkyl, which is then reacted with a suitable halogenating agent such as a N-halo-amide, perchloryl fluoride to produce the desired compound III.

2. A compound of the structure:

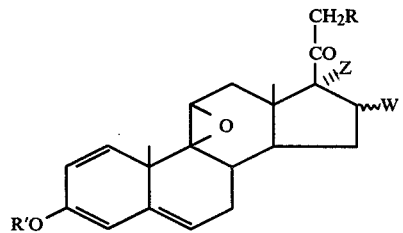

wherein R,Z and W have the above meaning and R' is a lower acyl or alkyl.

3. 3,21-diacetoxy-9β,11β-oxido-16α,17α-dihydroxypregna-1,3,5-triene-20-one 16,17-acetonide.

4. 3-Methoxy-9β,11β-oxido-16α,17α,21-trihydroxypregna-1,3,5-triene-20-one 16,17-acetonide 21-acetate.

5. 3,17,21-Triacetoxy-9β,11β-oxido-16α-methylpregna-1,3,5-triene-20-one.

6. 3,17,21-Triacetoxy-9β,11β-oxido-16β-methylpregna-1,3,5-triene-20-one.

7. 3,17-Diacetoxy-9β,11β-oxido-16β-methylpregna-1,3,5-triene-20-one.

8. 3-Methoxy-9β,11β-oxido-17α,21-dihydroxy-16α-methylpregna-1,3,5-triene-20-one 21-trimethylacetate.

9. 3,21-Diacetoxy-9β,11β-oxido-16α-methylpregna-1,3,5-triene-20-one.

* * * * *